(12) United States Patent
Hopper et al.

(10) Patent No.: US 9,069,098 B2
(45) Date of Patent: Jun. 30, 2015

(54) THREE OR MORE MULTIPLE FIGURE-EIGHT COILS FOR NMR WELL-LOGGING MEASUREMENTS WITH AZIMUTHAL DIRECTIONAL SENSITIVITY

(75) Inventors: Timothy Hopper, Shenton Park (AU); David G. Cory, Branchton (CA); Yi-Qiao Song, Newton, MA (US); Martin D. Hurlimann, Newton, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 660 days.

(21) Appl. No.: 13/228,715

(22) Filed: Sep. 9, 2011

(65) Prior Publication Data

US 2013/0063142 A1   Mar. 14, 2013

(51) Int. Cl.
*G01V 3/32* (2006.01)
*G01R 33/3415* (2006.01)
*G01N 24/08* (2006.01)

(52) U.S. Cl.
CPC ............... *G01V 3/32* (2013.01); *G01N 24/081* (2013.01); *G01R 33/3415* (2013.01)

(58) Field of Classification Search
USPC .......................... 324/300–322; 600/407–435; 382/128–131
See application file for complete search history.

(56) References Cited

U.S. PATENT DOCUMENTS

| | | | |
|---|---|---|---|
| 5,629,623 A | | 5/1997 | Sezginer et al. |
| 6,246,236 B1 * | | 6/2001 | Poitzsch et al. ............... 324/303 |
| 6,268,726 B1 * | | 7/2001 | Prammer et al. ............. 324/303 |
| 6,291,995 B1 * | | 9/2001 | Speier et al. .................. 324/303 |
| 6,856,132 B2 * | | 2/2005 | Appel et al. .................. 324/303 |
| 7,012,426 B2 * | | 3/2006 | Edwards et al. .............. 324/303 |
| 7,227,355 B2 * | | 6/2007 | Chen et al. .................... 324/303 |
| 7,295,005 B2 * | | 11/2007 | Edwards ....................... 324/303 |
| 7,659,719 B2 * | | 2/2010 | Vaughan et al. .............. 324/318 |
| 7,852,074 B2 * | | 12/2010 | Edwards ....................... 324/303 |
| 8,188,740 B2 * | | 5/2012 | Ninomiya et al. ............ 324/318 |

(Continued)

FOREIGN PATENT DOCUMENTS

RU    2369406    10/2009

OTHER PUBLICATIONS

International Search Report and Written Opinion of the International Searching Authority for App. No. PCT/US2012/053461 dated Dec. 6, 2012 (6 pages).
"Chapter 27: Introduction to MRI Coils and Magnets", Physical Principals and Sequence Design, pp. 827-861.

(Continued)

*Primary Examiner* — Melissa Koval
*Assistant Examiner* — Tiffany Fetzner
(74) *Attorney, Agent, or Firm* — Mark D. Shelley, II

(57) ABSTRACT

An NMR apparatus disposed in a wellbore and having an array of two or more NMR sensors located at substantially the same axial position on the NMR apparatus and having different directional sensitivities is used to acquire an NMR signal from at least two of the two or more NMR sensors. The NMR signals are combined to obtain borehole information. The borehole information may include an azimuthal image of the formation surrounding the borehole. The azimuthal image may be a formation porosity image, a formation bound fluid image, a T2 distribution image, a T2 log mean image, a formation permeability image, or a formation fluid viscosity image. If two or more pre-amplifiers and receiver circuitry are also provided, the NMR signals may be combined prior to passing through the pre-amplifiers and receiver circuitry to improve the signal to noise ratio of the total signal from the desired sample space.

19 Claims, 6 Drawing Sheets

SINGLE

MULTIPLE COILS

(56) References Cited

U.S. PATENT DOCUMENTS

| | | | |
|---|---|---|---|
| 8,324,895 B2* | 12/2012 | Rottengatter | 324/303 |
| 8,373,412 B2* | 2/2013 | Kruspe et al. | 324/303 |
| 8,384,379 B2* | 2/2013 | Nielsen et al. | 324/303 |
| 2002/0180435 A1 | 12/2002 | Edwards et al. | |
| 2004/0090230 A1* | 5/2004 | Appel et al. | 324/307 |
| 2004/0183533 A1 | 9/2004 | Edwards et al. | |
| 2006/0132129 A1* | 6/2006 | Edwards | 324/303 |
| 2010/0188080 A1* | 7/2010 | Kruspe et al. | |
| 2013/0063142 A1* | 3/2013 | Hopper et al. | 324/303 |

OTHER PUBLICATIONS

Hayes, et al., "Noise correlations in data simultaneously acquired from multiple surface coil arrays", Magnetic Resonance in Medicine, vol. 16, 1990, pp. 181-191.

Jin, Jianming, "Electromagnetic Analysis and Design in Magnetic Resonance Imaging", Department of Electrical and Computer Engineering, University of Illinois at Urbana-Champaign, Urbana, Illinois, CRC Press, 5 pages.

King, et al., "Eigenmode Analysis for Understanding Phased Array Coils and Their Limits", Concepts in Magnetic Resonance Part B, vol. 29B (1), 2006, pp. 42-49.

* cited by examiner

SINGLE        MULTIPLE COILS

THREE OR MORE MULTIPLE FIGURE-EIGHT COILS FOR NMR WELL-LOGGING MEASUREMENTS WITH AZIMUTHAL DIRECTIONAL SENSITIVITY

CROSS-REFERENCE TO RELATED APPLICATIONS

N/A

BACKGROUND OF THE DISCLOSURE

Nuclear Magnetic Resonance (NMR) tools used for well-logging or downhole fluid characterization measure the response of nuclear spins in formation fluids to applied magnetic fields. Downhole NMR tools typically have a permanent magnet that produces a static magnetic field at a desired test location (e.g., where the fluid is located). The static magnetic field produces a magnetization in the fluid. The magnetization is aligned along the direction of the static field. The magnitude of the induced magnetization is proportional to the magnitude of the static field. A transmitter antenna produces a time-dependent radio frequency magnetic field that has a component perpendicular to the direction of the static field. The NMR resonance condition is satisfied when the radio frequency is equal to the Larmor frequency, which is proportional to the magnitude of the static magnetic field. The radio frequency magnetic field produces a torque on the magnetization vector that causes it to rotate about the axis of the applied radio frequency field. The rotation results in the magnetization vector developing a component perpendicular to the direction of the static magnetic field. This causes the magnetization vector to precess around the static field at the Larmor frequency. At resonance between the Larmor and transmitter frequencies, the magnetization is tipped to the transverse plane (i.e., a plane normal to static magnetic field vector). A series of radio frequency pulses are applied to generate spin echoes that are measured with the antenna.

NMR measurements can be used to estimate, among other things, formation porosity and formation permeability. For example, the area under the curve of a T2 distribution for a NMR measurement equals the NMR porosity. The T2 distribution also resembles the pore size distribution in water-saturated rocks. The raw reported porosity is provided by the ratio of the initial amplitude of the raw decay and the tool response in a water tank. This porosity is independent of the lithology of the rock matrix.

The NMR estimate of permeability is based on a theoretical model such as the Free-fluid (Coates) model or the average-T2 model. The Free-fluid model can be applied in formations containing water and/or hydrocarbons, while the average-T2 model can be applied to pore systems containing water only. Measurements on core samples are generally required to refine and customize those models for local use. The NMR permeability tends to increase with both increasing porosity and increasing pore size.

Crude oil properties such as viscosity, molecular composition, gas-oil ratio, and SARA (saturates, aromatics, resins, asphaltenes) fractions are crucial parameters for evaluating, for example, reservoir quality, producibility, and compartmentalization. Physical and empirical model-based equations have been developed which relate the properties of crude oils to Nuclear Magnetic Resonance (NMR) measurements. NMR response of fluids provides a link between microscopic molecular motions and macroscopic properties such as viscosity and composition. The relationship between viscosity and relaxation time of pure fluids was established by the phenomenological relaxation theory of Bloembergen, Purcell, and Pound (BPP). Brown studied proton relaxation in a suite of crude oils with various compositions and viscosities. The viscosities of the samples varied from about 0.5 to 400 cp. He found that the relaxation times showed an inverse dependence on viscosity over the entire range. Since the early work of Brown, several physical and empirical models have been proposed that relate crude oil properties to NMR response. Understanding of molecular dynamics in alkane mixture resulted in the establishment of a scale-law theory to relate NMR diffusion and relaxation properties to the molecular composition of crude oils. There are also other database approaches such as, for example, Artificial Neural Networks (ANN) and Radial Basis Function.

Characterization of reservoir fluids is crucial for several aspects of reservoir development and management. For example, fluid properties such as viscosity and molecular composition are used to calculate flow rates and sweep efficiencies of secondary and tertiary recoveries. Gas-oil ratio (GOR) of reservoir fluids is an important parameter for material selection of well completion and design of surface facilities. Asphaltene and wax concentrations are key considerations for flow assurance in completions, pipelines, and surface facilities. Estimation of fluid properties at different depths in a reservoir provides indications of compositional grading and compartmentalization within the reservoir. It is useful to obtain fluid properties from measurements such as NMR well-logging which can be performed at downhole temperature and pressure conditions.

Borehole images allow one to interpret the rock record for oil and gas exploration. In addition to identifying fractures and faults, borehole imaging tools are used for a variety of other applications such as sequence stratigraphy, facies reconstruction, stratigraphy, and diagenetic analysis. They can be used in a wide variety of geological and drilling environments, providing high resolution borehole images of rock and fluid properties in formations ranging from fractured carbonates to soft, thinly laminated sand/shale sequences. These tools produce high resolution and often nearly complete borehole coverage, which may be interpreted at an interactive graphics workstation.

NMR well-logging tools differ from those commonly used in the medical field in many respects. Obviously the operating environment for a downhole tool is much harsher than the laboratory setting of an imaging facility. In addition, a downhole NMR is configured "inside-out" relative to a typical "closed" medical NMR device. That is, medical devices usually look inward to their targeted area, whereas downhole NMR devices look outward into the surrounding formation.

SUMMARY

An NMR apparatus disposed in a wellbore and having an array of two or more NMR sensors located at substantially the same axial position on the NMR apparatus and having different directional sensitivities is used to acquire an NMR signal from at least two of the two or more NMR sensors. The NMR signals are combined to obtain borehole information. The borehole information may include an azimuthal image of the formation surrounding the borehole. The azimuthal image may be a formation porosity image, a formation bound fluid image, a T2 distribution image, a T2 log mean image, a formation permeability image, or a formation fluid viscosity image If two or more pre-amplifiers and receiver circuitry are also provided on the NMR apparatus, the NMR signals may be combined prior to passing through the pre-amplifiers and receiver circuitry to improve the signal to noise ratio of the total signal from the desired sample space.

BRIEF DESCRIPTION OF THE DRAWINGS

The present disclosure is best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over or on a second feature in the description that follows may include embodiments in which the first and second features are formed in direct contact, and may also include embodiments in which additional features may be formed interposing the first and second features, such that the first and second features may not be in direct contact.

Figure 1:
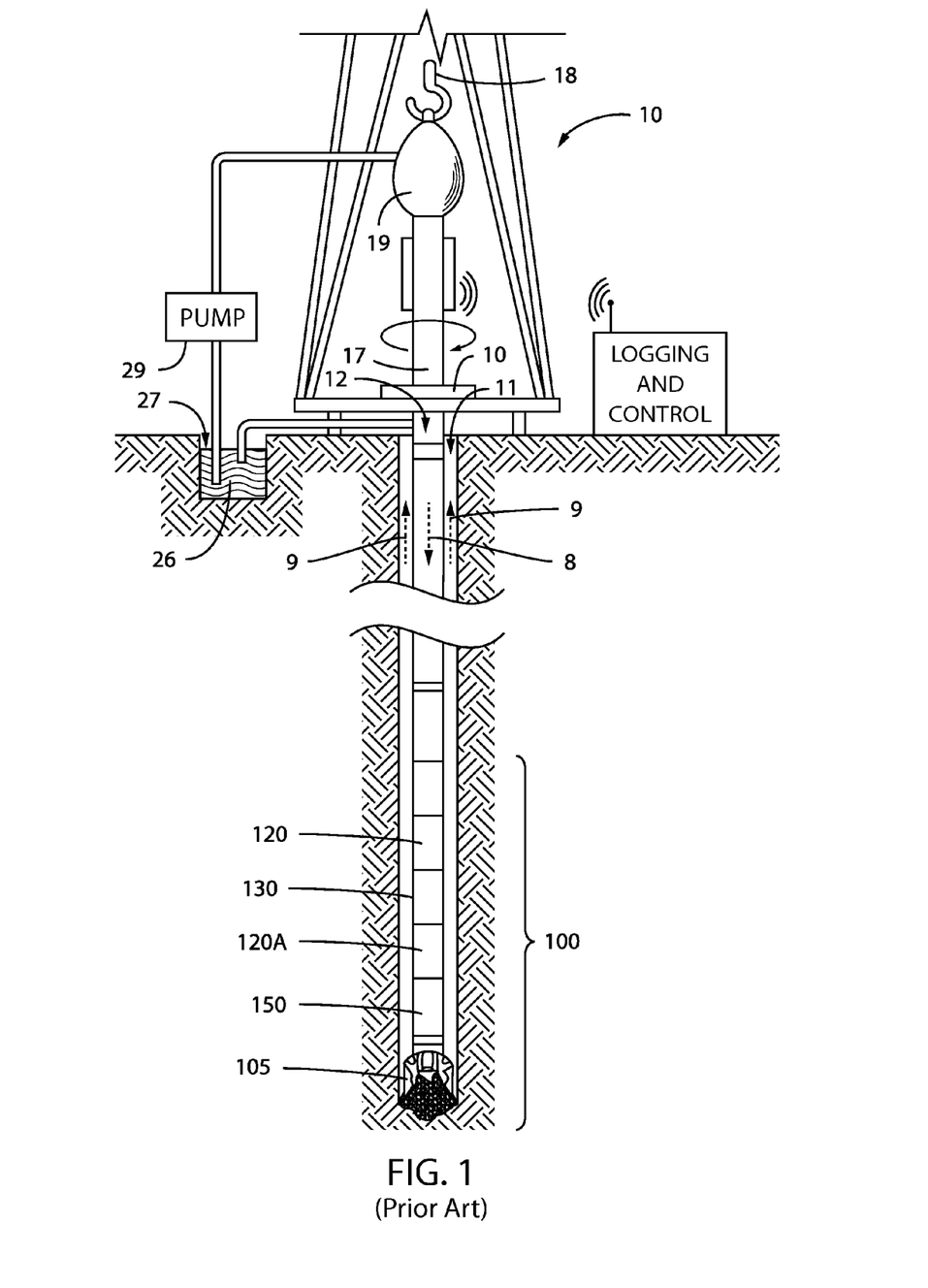
FIG. 1 illustrates an exemplary well site system.

FIG. 1 illustrates a well site system in which various embodiments can be employed. The well site can be onshore or offshore. In this exemplary system, a borehole 11 is formed in subsurface formations by rotary drilling in a manner that is well known. Some embodiments can also use directional drilling, as will be described hereinafter.

A drill string 12 is suspended within the borehole 11 and has a bottom hole assembly 100 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could alternatively be used.

In the example of this embodiment, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this well known manner, the drilling fluid lubricates the drill bit 105 and carries formation cuttings up to the surface as it is returned to the pit 27 for recirculation.

The bottom hole assembly 100 of the illustrated embodiment includes a logging-while-drilling (LWD) module 120, a measuring-while-drilling (MWD) module 130, a roto-steerable system and motor 150, and drill bit 105.

The LWD module 120 is housed in a special type of drill collar, as is known in the art, and can contain one or a plurality of known types of logging tools. It will also be understood that more than one LWD and/or MWD module can be employed, e.g. as represented at 120A. (References, throughout, to a module at the position of 120 can alternatively mean a module at the position of 120A as well.) The LWD module includes capabilities for measuring, processing, and storing information, as well as for communicating with the surface equipment. In the present embodiment, the LWD module includes a NMR measuring device.

The MWD module 130 is also housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick/slip measuring device, a direction measuring device, and an inclination measuring device.

Figure 2:
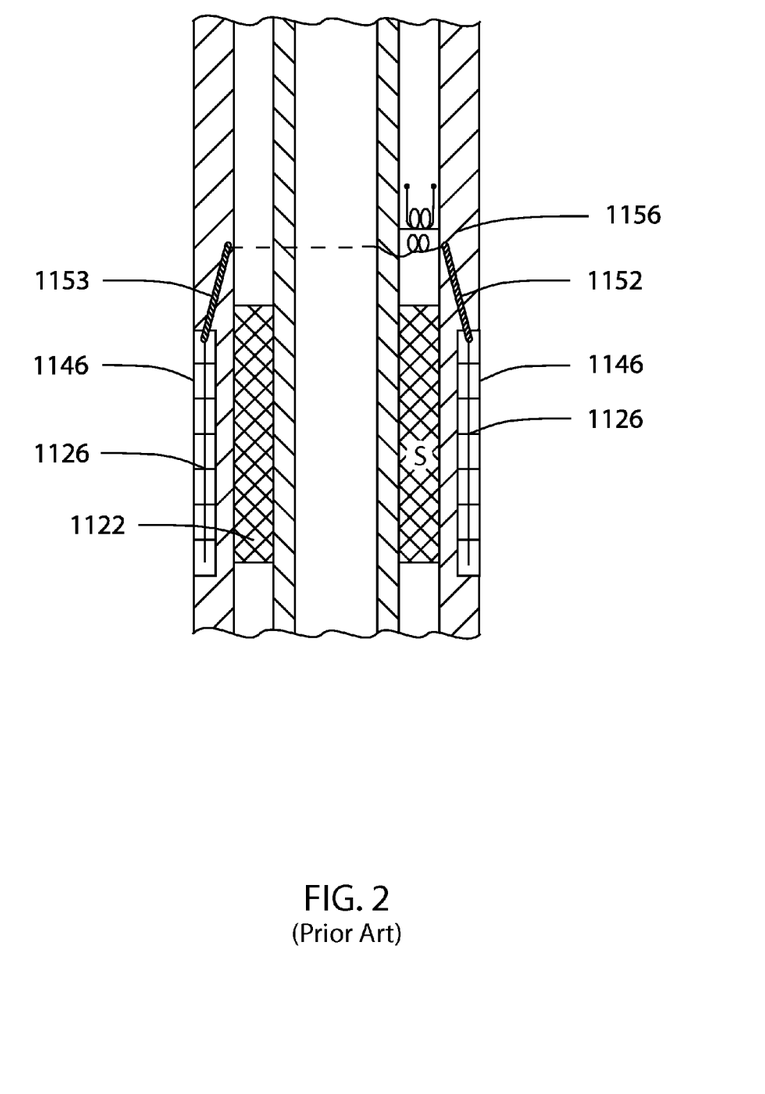
FIG. 2 shows a prior art nuclear magnetic resonance logging tool.

FIG. 2 shows an embodiment of a type of device described in U.S. Pat. No. 5,629,623 for formation evaluation while drilling using pulsed nuclear magnetic resonance (NMR), incorporated herein by reference, it being understood that other types of NMR/LWD tools can also be utilized as the LWD tool 120 or part of an LWD tool suite 120A. As described in the '623 Patent, an embodiment of one configuration of the device comprises a modified drill collar having an axial groove or slot that is filled with a ceramic insulator, and contains RF antenna 1126, which is protected by a non-magnetic cover 1146 and produces and receives pulsed RF electromagnetic energy. In the embodiment shown, the conductors of the RF antenna are grounded at one end to the drill collar. At the other end, the conductors are coupled to an RF transformer 1156 via pressure feed-throughs 1152 and 1153. A cylindrical magnet 1122 produces a static magnetic field in the formations. The RF antenna can also be arranged so that the drill collar itself produces the oscillating RF magnetic field. The oscillating RF magnetic field, which excites nuclei of substances in the formations, is axially symmetric, to facilitate measurements during rotation of the drill string.

Magnetic Resonance Imaging involves the spatial localization of protons within a sample space. One possible imaging technique involves the use of multiple receiver coils placed in an array. Each coil receives signal from a localized area that can be reconstructed into an image covering the region of interest. Thus, it is possible to obtain an azimuthal image of some aspect of the sample space.

Figure 3:
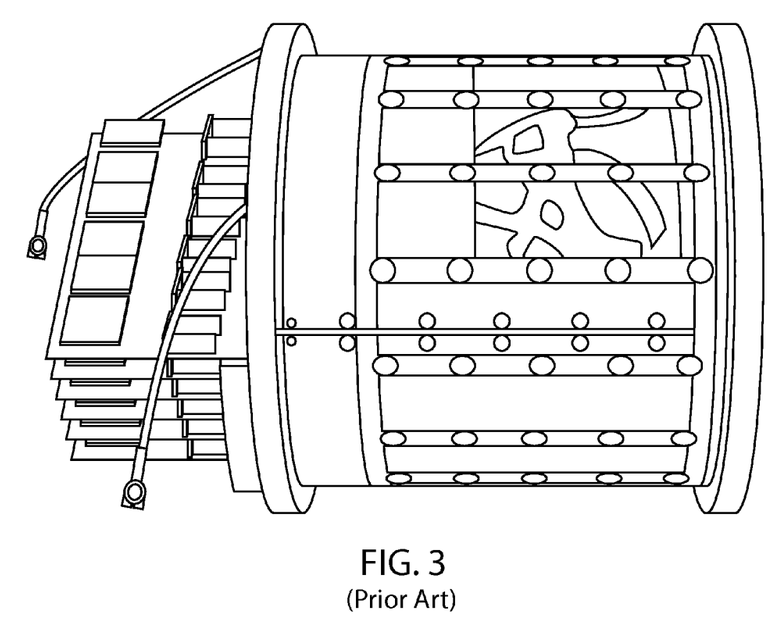
FIG. 3 shows an example prior art Magnetic Resonance Imaging (MRI) coil typically used in a laboratory.

FIG. 3 shows an exemplary prior art MRI (magnetic resonance imaging) antenna typically used in a laboratory setting. This antenna is a "phased array" antenna made up of a series of rectangular coils overlapping each other by an optimal distance. The coil arrangement is optimized to reduce mutual coupling.

A small surface coil generally provides a lower noise level than a large coil because the smaller coil has a smaller sensitive region and thus, the amount of noise received from that smaller sensitive region is less than the amount of noise received by the larger coil since the larger coil receives signal from the entire sample. Since each coil is designed to receive signal from a different region, we denote the signal from coil i to be $S_i$. Since the spatial arrangement of the coils is known by the design of the coils, the signal $S_i$ directly determines the spatial distribution of the NMR signal. Analysis of the signals can produce an image of the borehole properties, such as T2 (distribution or log mean), porosity, permeability, bound and free fluids, and crude oil properties.

The signals of multiple coils can also be combined to measure the properties of the entire borehole sample. In one embodiment, the individually detected (digitized) signals from all coils can be added at the post-processing stage to obtain the signal of the entire borehole. This post-processing will further enhance the SNR (signal-to-noise ratio) compared to the SNR of an individual coil. This is because the noises from different coils are generally uncorrelated (assuming the coils are mutually decoupled and they measure a different region in space), while the signals are additive. The total signal from the entire sample space is then: $S_{total}=S_1+S_2+\ldots+S_N=S*N$, where N is the total number of coils, and S is the signal amplitude of each small coil. However, the noise adds as: $N_{total}=\text{Sqrt}(n_1\hat{0}2+n_2\hat{\;}2+\ldots+n_N\hat{0}2).=n*\text{Sqrt}(N)$, where $n_i$ is the noise of each coil and n is the amplitude of the noise from the small coil. Here we assume the smaller coils are all the same and thus the noise amplitude is the same. Thus the final SNR of the entire sample is sqrt(N)*S/n, and the enhancement of SNR is sqrt(N).

In practice, if each coil has its own receiver electronics which includes a deplexer, a low-noise pre-amplifier front end, and an additional signal gain and digitization system, the receiver electronics will contribute additional noise to the signal. We shall denote the amplitude of this noise to be $n_d$. As a result, in practice, the design of multiple coils with their individual receivers may not achieve the theoretical SNR enhancement of sqrt(N). One way to combine the signals from the small coils without losing SNR is to connect all the coils in series or in parallel before delivering their outputs to the receiver electronics. This avoids the addition of the individual receiver noises ($n_d$) and it increases the signal amplitude before it enters the receiver electronics. The total noise amplitude of the combined signal can be significantly larger than that of the individual coil, for example, by sqrt(N), so that the relative contribution of the receiver electronic noise ($n_d$) is much reduced.

Excitation of the transmitter coils can be achieved in at least two ways. The coils can be excited in series, whereby they effectively act as one coil, or each coil can be independently excited (in parallel). The coils may be tuned or left un-tuned. When transmitting in series and receiving in parallel, the coil is generally called a "uncoil".

It is also possible to design the coil assembly to include a transmitter coil to be used to excite the entire sample region while the signal reception is performed by the array of smaller coils. This technique separates the transmission and reception coils and may include electronics (e.g., a deplexer) to protect the reception coils and the receiver electronics during the transmission of the strong RF pulses.

Detection may be achieved through each coil independently of the other coils. One possible embodiment is to have each coil with its own tank circuit, duplexer, pre-amplifier, and receiver. This way, the signal from each coil can be processed and then added later. In the case of downhole NMR applications, a sum of the signals from all the receiver coils will yield the total porosity, T2, or other parameters. If the signals are kept separate, they can be processed to provide an azimuthal image. This image could be based on porosity or bound fluid or some other identifier.

Figure 4:
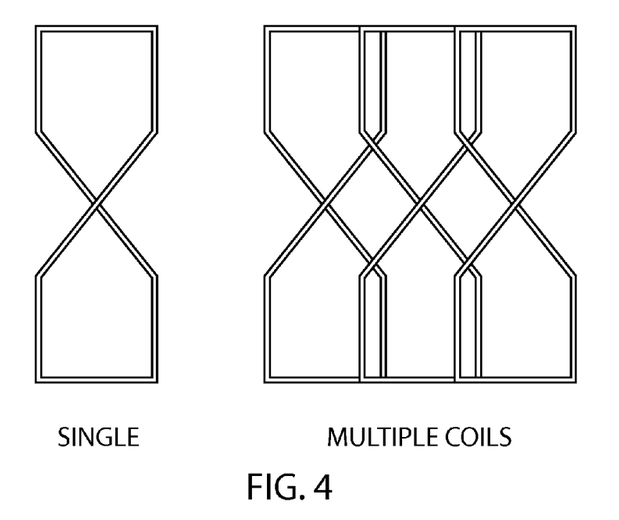
FIG. 4 schematically shows a single "Figure 8" style coil and a set of multiple (three "Figure 8" style) coils in an array, in accordance with the present disclosure.

FIG. 4 schematically shows a single "Figure 8" style coil and a set of multiple (three "Figure 8" style) coils in an array. As can be seen in FIG. 4, the coils overlap with each other.

Figure 5A:
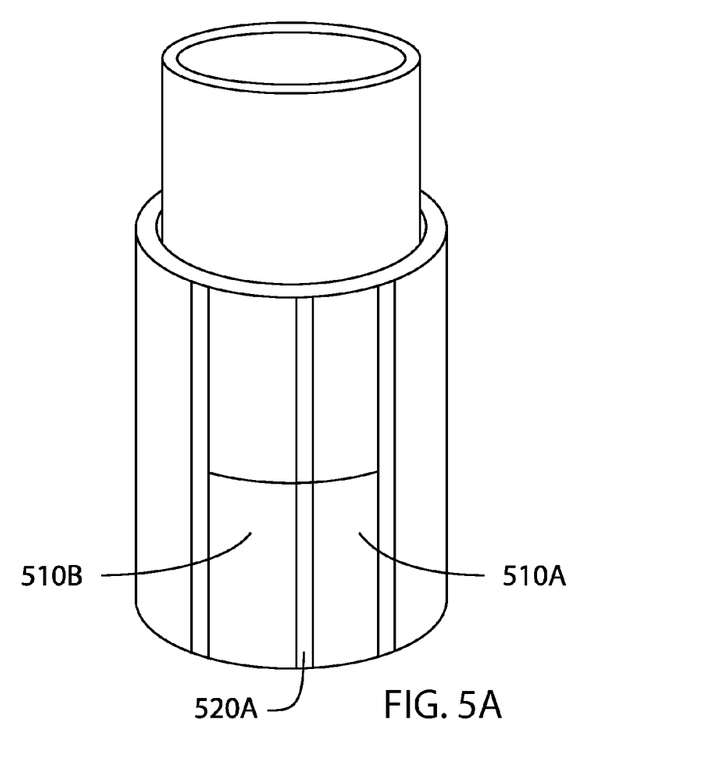
FIGS. 5A and 5B shows an embodiment of a phased array antenna for use in a downhole NMR tool, in accordance with the present disclosure.
Figure 5B:
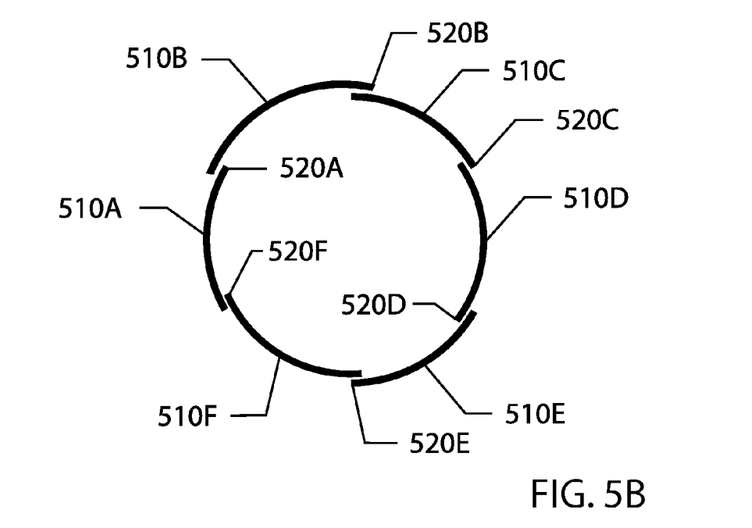

FIGS. 5A and 5B show an embodiment of a phased array antenna for use in a downhole NMR tool. As shown in the side view schematic of FIG. 5A and the top view schematic of FIG. 5B, the phased array antenna includes six separate coils 510A-F, all overlapping each other at overlap points 520A-F.

Figure 6:
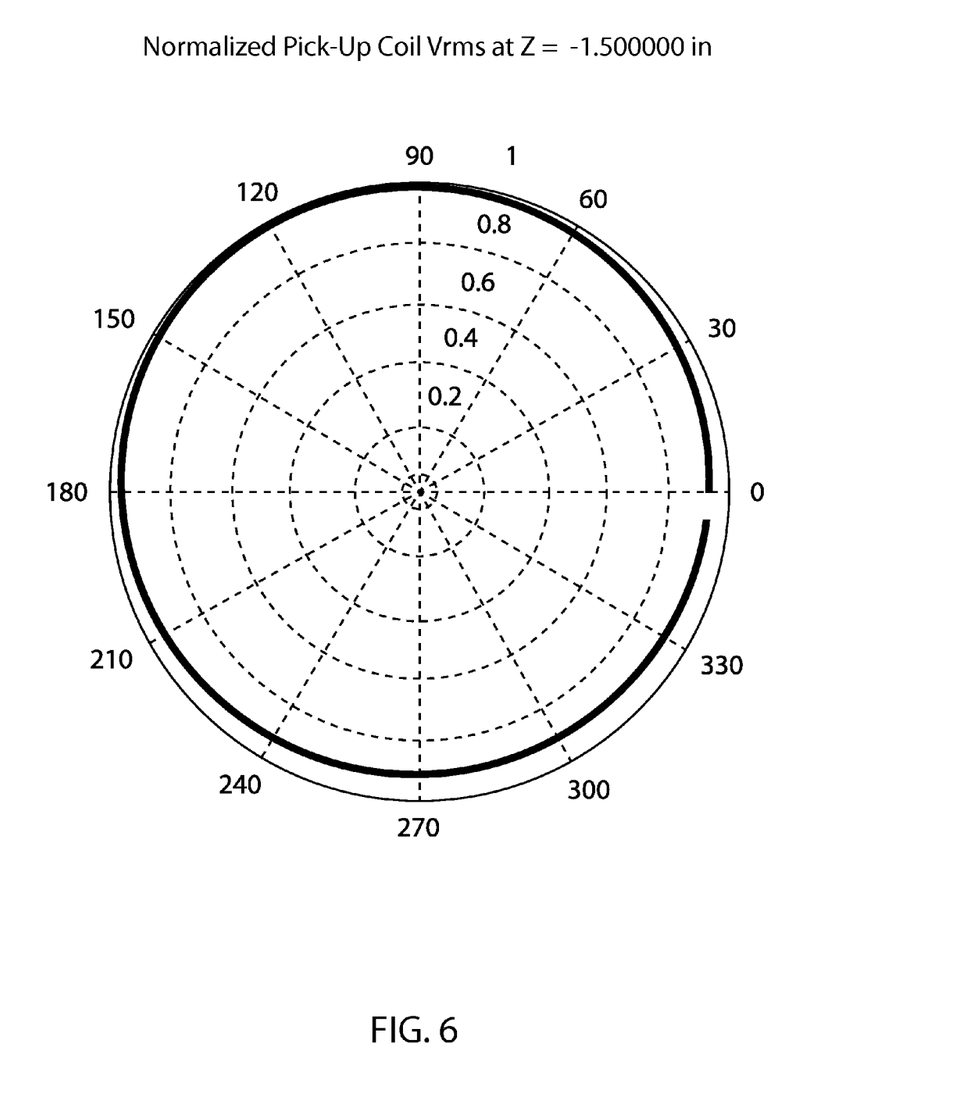
FIG. 6 is a plot of radio frequency (RF) field measurements of the B1 field generated when the coils are fired in series, in accordance with the present disclosure.

FIG. 6 is a plot of radio frequency (RF) field measurements of the B1 field generated when the coils are fired in series. The plot shows the homogeneity of the field.

The signals from each coil can also be combined prior to the pre-amplifier and receiver circuitry. This simplifies the operation of the entire setup, but the data would no longer provide a image. It would however, further increase the SNR.

Figure 7:
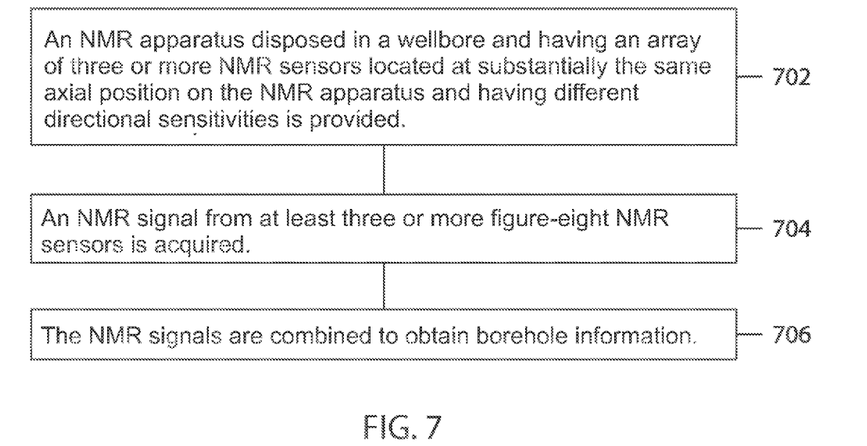
FIG. 7 is a flowchart of at least a portion of a method, according to one or more aspects of the present disclosure.

FIG. 7 shows a flowchart illustrating an embodiment in accordance with this disclosure. An NMR apparatus disposed in a wellbore and having an array of two or more NMR sensors located at substantially the same axial position on the NMR apparatus and having different directional sensitivities is provided (step 702). An NMR signal from at least two of the two or more NMR sensors is acquired (step 704). The NMR signals are combined to obtain borehole information (step 706).

Figure 8:
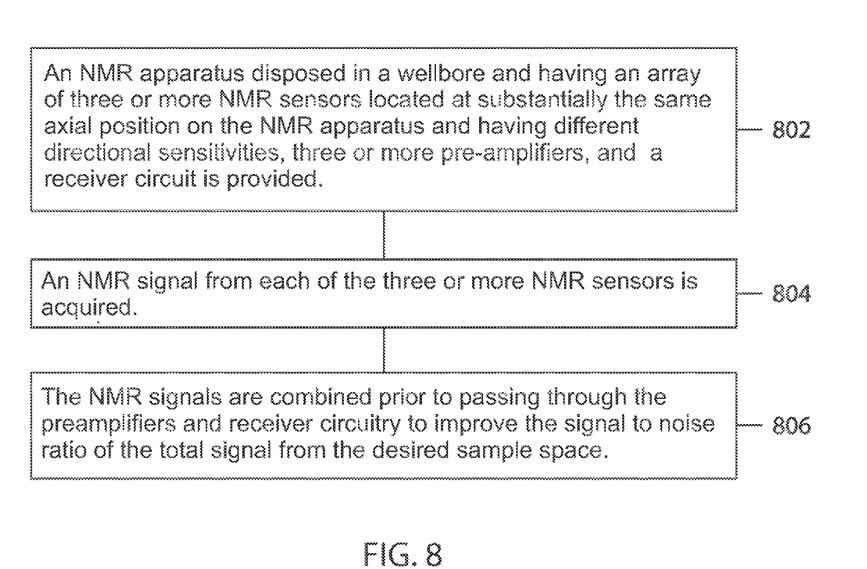
FIG. 8 is a flowchart of at least a portion of a method, according to one or more aspects of the present disclosure.

FIG. 8 shows a flowchart illustrating an embodiment in accordance with this disclosure. An NMR apparatus disposed in a wellbore and having an array of two or more NMR sensors located at substantially the same axial position on the NMR apparatus and having different directional sensitivities, two or more pre-amplifiers, and receiver circuit is provided (step 802). An NMR signal from each of the two or more NMR sensors is acquired (step 804). The NMR signals are combined prior to passing through the pre-amplifiers and receiver circuitry to improve the signal to noise ratio of the total signal from the desired sample space (step 806).

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the scope of the present disclosure, and that they may make various changes, substitutions, and alterations herein without departing from the scope of the present disclosure.

The Abstract at the end of this disclosure is provided to comply with 37 C.F.R. §1.72(b) to allow the reader to quickly ascertain the nature of the technical disclosure. It is submitted with the understanding that it will not be used to interpret or limit the scope or meaning of the claims.

What is claimed is:

1. An NMR method, comprising:
providing an NMR apparatus disposed in a wellbore and having an array of three or more figure-eight coil NMR sensors, wherein the NMR apparatus has an axial length aligned with a wellbore trajectory and the figure-eight coil NMR sensors are located at substantially the same axial length position along the axial length of the NMR apparatus and having different azimuthally directional sensitivities, and wherein a first figure-eight coil of the three or more figure-eight coil NMR sensors overlaps a second figure-eight coil of the three or more figure-eight coil NMR sensors at a first axial length position of the NMR apparatus and wherein the second figure-eight coil of the three or more figure-eight coil NMR sensors overlaps a third figure-eight coil of the three or more figure-eight coil NMR sensors at the first axial length position of the NMR apparatus; acquiring an NMR signal from at least three of the three or more figure-eight coil NMR sensors; and combining the NMR signals in order to obtain an azimuthal image of the borehole.

2. The method of claim 1, providing a transmitter separate from the array of three or more figure-eight coil NMR sensors, and comprising transmitting using the transmitter and acquiring the NMR signal based on the transmission by the transmitter.

3. The method of claim 1, wherein the acquiring comprises energizing some or all of the NMR sensors that are electronically configured to be in series in order to transmit a signal into the desired sample space, and receiving the signals from the desired sample space by some or all of the NMR sensors that are electronically configured to be in parallel.

4. The method of claim 3, wherein the NMR sensors are switchable between series and parallel electronic configurations.

5. The method of claim 1, wherein the acquiring comprises detecting the NMR signal at each NMR sensor independently from the other NMR sensors.

6. The method of claim 1, wherein the combining comprises adding the NMR signals.

7. The method of claim 1, comprising steering a drill bit based on the azimuthal image of the borehole.

8. The method of claim 1, wherein the NMR sensors are not tuned.

9. The method of claim 7, wherein steering the drill bit comprises steering the drill bit, wherein the drill bit comprises a roto-steerable drill bit.

10. The method of claim 1, wherein the azimuthal image comprises a formation porosity image, a formation bound fluid image, a T2 distribution image, a T2 log mean image, a formation permeability image, or a formation fluid viscosity image.

11. The method of claim 1, comprising using the NMR signals in order to obtain borehole information that includes non-azimuthal formation properties, non-azimuthal fluid properties, or both.

12. The method of claim 1, comprising shaping a radio frequency field using the three or more figure-eight coil NMR sensors.

13. The method of claim 1, comprising changing the resonance frequency of one or more of the three or more figure-eight coil NMR sensors.

14. The method of claim 1, wherein at least one of the three or more figure-eight coil NMR sensors has a different resonance frequency.

15. The method of claim 1, wherein the combining comprises increasing the signal to noise ratio of the total signal from a desired sample space.

16. A nuclear magnetic resonance (NMR) system, comprising:
an NMR apparatus having an axial length configured to align with a wellbore trajectory and configured to be disposed in a wellbore and having an array of three or more figure-eight coil NMR sensors, wherein a first figure-eight coil of the three or more figure-eight coil NMR sensors overlaps a second figure-eight coil of the three or more figure-eight coil NMR sensors at a first axial length position of the NMR apparatus and wherein the second figure-eight coil of the three or more figure-eight coil NMR sensors overlaps a third figure-eight coil of the three or more figure-eight coil NMR sensors at the first axial length position of the NMR apparatus, wherein each of the three or more figure-eight coil NMR sensors has a different azimuthally directional sensitivity; and
a processor configured to cause acquiring of an NMR signal from each of the three or more NMR sensors and configured to combine the NMR signals in order to obtain borehole information.

17. NMR system of claim 16, wherein the processor is configured to generate an azimuthal image using the borehole information.

18. The NMR system of claim 16, wherein the processor is configured to generate non-azimuthal formation properties, non-azimuthal fluid properties, or both, using the borehole information.

19. An NMR method, comprising:
providing an NMR apparatus having an axial length aligned with a trajectory of a wellbore when disposed in the wellbore, wherein the NMR apparatus comprises:
an array of three or more figure-eight coil NMR sensors, wherein a first figure-eight coil of the three or more figure-eight coil NMR sensors overlaps a second figure-eight coil of the three or more figure-eight coil NMR sensors at a first axial length position of the NMR apparatus and wherein the second figure-eight coil of the three or more figure-eight coil NMR sensors overlaps a third figure-eight coil of the three or more figure-eight coil NMR sensors at the first axial length position of the NMR apparatus, wherein each of the three or more figure-eight coil NMR sensors has a different azimuthally directional sensitivity and wherein the NMR apparatus comprises three or more pre-amplifiers, and receiver circuitry;
acquiring an NMR signal from each of the three or more NMR sensors; and
combining the NMR signals prior to passing through the pre-amplifiers and receiver circuitry in order to improve the signal to noise ratio of the total signal from a desired sample space.

* * * * *